United States Patent [19]

Tronconi

[11] Patent Number: 5,250,719
[45] Date of Patent: Oct. 5, 1993

[54] PROCESS FOR THE PREPARATION OF L-α-GLYCERYLPHOSPHORYL-CHOLINE AND OF L-α-GLYCERYLPHOSPHORYLETHANOLAMINE

[75] Inventor: Giovanni Tronconi, Grato-Lodi, Italy

[73] Assignee: Prime European Therapeuticals S.p.A., Lodi, Italy

[21] Appl. No.: 773,923

[22] PCT Filed: May 4, 1990

[86] PCT No.: PCT/EP90/00717
§ 371 Date: Nov. 8, 1991
§ 102(e) Date: Nov. 8, 1991

[87] PCT Pub. No.: WO90/13552
PCT Pub. Date: Nov. 15, 1990

[30] Foreign Application Priority Data

May 8, 1989 [IT] Italy .................. 20413 A/89

[51] Int. Cl.$^5$ ................ C07F 9/10
[52] U.S. Cl. .................... 558/146
[58] Field of Search ................ 558/146

[56] References Cited

FOREIGN PATENT DOCUMENTS 217705  4/1987  European Pat. Off. .
1543722 4/1969  Fed. Rep. of Germany .

OTHER PUBLICATIONS

Kaitaranta J. Chrom. 206, 327 (1981).

Primary Examiner—Robert Gerstl
Attorney, Agent, or Firm—Walter H. Schneider

[57] ABSTRACT

A process for the purification of glycerylphosphorylcholine (GPC) and glycerylphosphorylethanolamine (GPE) from crude mixtures by eluting the latter on a cationic resin in acid form equilibrated in an anhydrous solvent, washing the resin with alcohol or a hydrated mixture thereof followed by washing with water, and then eluting on a strong basic resin in OH form to separate purified GPC and GPE.

5 Claims, No Drawings

PROCESS FOR THE PREPARATION OF L-α-GLYCERYLPHOSPHORYL-CHOLINE AND OF L-α-GLYCERYLPHOSPHORYLETHANOLAMINE

The present invention refers to a method for the preparation of L-α-glycerylphosphorylcholine (GPC) and of L-α-glycerylphosphorylethanolamine (GPE) with very high yields and purity, using as starting materials lecithins of different origin.

The known methods for the preparation of GPC are not suited to the industrial application or yield GPC at very high cost because of the difficulties involved in the purification by crystallisation.

The crystallisation of GPC is infact reliable and gives good yields only when the product itself is already very pure, otherwise, as also reported in Biochem. Preparations 6, 16, 1958, either GPC cannot be purified or the crystallisation yields are very low. In the above cited reference, for instance, the authors use crude egg lecithin but purify GPC by crystallising the complex with cadmium chloride.

The removal of the very toxic $CdCl_2$ asks for a treatment on high amounts of ion-exchange resins, causing a marked decrease of yeld of pure GPC and preventing the large scale application.

C. Cubrero et al in Chem. Phys Lipids 6, 31, 1971, obtain pure GPC by silica gel chromatography.

This process is very expensive and difficult to apply industrially and gives GPC impure with silicic acid.

DE-A-1,543,722 discloses a method for the recovery of pure, naturally occurring phospholipids from crude lecithins by passing a solution of the crude starting material over a silica gel column and eluting with a mixture of toluene and methanol.

GB 2058792 discloses a process for the preparation of GPC in high purity and suited for large scale operations.

This process circumvents the difficulties of the GPC purification using as starting material very pure phosphatidylcholine. No purification of the obtained GPC is carried out (except the removal of fatty acid esters released in the deacylation of phosphatidylcholine), but the use of very pure and expensive phosphatidylcholine limits the utility of the process which cannot be used, of course, with crude soy or egg lecithins or even with phosphatidylcholine not completely free from other phosphatides or other neutral or acidic hydrosoluble impurities.

EP-A-217765 discloses a process for the preparation of GPC and GPE from crude or deoleated soy lecithins or from crude egg lecithin, through a pure complex of formula $(nGPC+mGPE) ZnCl_2$ wherein n and m have values from 0 to 1 and $m+n=1$. The zinc chloride is then eliminated by means of the water insoluble complex $ZnCl_2Py_2$ (Py=pyridine) obtaining a water solution of $nGPC+mGPE$ which is then separated on ion-exchange resins. In order to obtain very pure GPC it is however necessary to carry out the deacylation on the ethanol extract of crude or deoleated soy lecithin, obtaining GPC with a yield of about 62% (calculated on the phosphatidylcholine content present in the deoleated soy lecithin).

An higher yield (about 95%) is obtained if the deacylation is carried out on the methanol extract or directly on the methanol suspension of crude or deoleated lecithin but the obtained product has a purity degree not suited for the pharmaceutical use and must be purified again by cumbersome procedure.

The process of the present invention allows the direct preparation of very pure GPC and GPE also from methanol extracts or suspension in high yields and conveniently.

The purification relies on the amphoteric character of GPC and GPE and comprises the elution on a cationic resin in acid form equilibrated in anhydrous solvent of the crude solutions from the deacylation step, washing the resin first with solvent and then with water.

During the elution of the crude deacylated solution in non aqueous medium, GPC, GPE and other basic substances are fixed on the resin, which may then be thoroughly washed with solvent, allowing the complete elimination of all the neutral and acidic impurities, without eluting GPC and GPE.

When the resin is washed with water, since GPC and GPE are very weak bases, the equilibrium between free and resin-bound bases is almost completely shifted towards the free bases, so that GPC and GPE are readily and quantitatively eluted.

The impurities more basic than GPC and GPE are also eliminated, such as ethanolamine and choline traces, because using cationic resins in acid form, these are eluted only using acidic or basic eluents, but not with water.

The purification of crude GPC/GPE mixtures on cationic resins in acid form is not known and asks for specific operative conditions (particular resin/solvent combinations) without which it is not possible to obtain stable bindings GPC/GPE-resin and it is not possible to avoid the strong degradation (sometimes complete) which GPC/GPE generally undergo in non aqueous medium on strong cationic resins in acid form whereas using said resins in aqueous medium the degradation is very poor or absent but it is not possible to obtain stable bindings and to carry out the purification.

For instance, in GB 2 058 792, a methanol solution of pure GPC is eluted on weak acidic resin but only to eliminate the sodium ion and the GPC is not bound quantitavely and irreversibly to the resin, because, as it will be explained hereinafter, the used combination resin/solvent does not allow to rely on the basicity of GPC/GPE and therefore the purification of the crude deacylated mixtures.

If, instead of an aqueous solution, a methanol solution of crude GPC and/or GPE is used, the carboxylic resins do not allow the purification since GPC and the mixture GPC/GPE are not bound in a stable way to the resin but are eluted together with impurities, whereas the sulfonic resins allow the formation of stable bindings between GPC/GPE-resin but generally cause a very high degradation of GPC because of cleavage of the P—O bond (up to complete degradation). The two hydroxy groups are involved in said degradation which in fact does not occurs when they are protected as esters or cyclic ketals.

When weak cationic resins are however used in ethanol, or some kinds of sulfonic resins having macroreticular structure in methanol, ethanol or their mixtures, GPC and GPE or mixtures $nGPC+mGPE$ in these conditions are bound irreversibly on the resins, forming mixtures which may be tentatively represented as:

$(nGPC+mGPE)\cdot p$ Resin wherein:
n represents mmoles of GPC and is ranging from 0 to 1 m represents mmoles of GPE and is ranging from 0 to 1 n+m=1 p represents mequivalents of resin and is ranging from 3 to 6 for strong cationic resins and from 6 to 8 for weak cationic resins.

Moreover, the degradation found when strong acid resins are used, can be avoided by keeping the mixture GPC+GPE absorbed on the resin for short periods, allowing therefore the purification according to the process of the invention, which may be generally described as follows.

The crude egg lecithin or the crude or deoleated soy lecithin in suspension or alcoholic solution (preferably in methanol or ethanol) is treated with an alkali metal alkoxide (preferably sodium or potassium methylate or ethylate).

The alcoholic solution containing the mixture nGPC+mGPE (n and m as above defined) is neutralized with an organic acid (preferably acetic or propionic acid) or with an inorganic acid (preferably hydrochloric, phosphoric or sulfuric acid) or by elution on small amounts of acid resin.

After concentration, most of fatty acid esters are removed by separating the two obtained phases and the alcoholic solution containing the mixture nGPC+mGPE is charged on an acid cationic resin (preferably a sulfonic resin of macroreticular type or a carboxylic resin) equilibrated in alcohols (preferably methanol, ethanol or mixtures thereof).

The mixture nGPC+mGPE so bound to the resin is then washed with alcohols (preferably methanol, ethanol or mixtures thereof) till complete elimination of the impurities present in the starting deacylation mixtures; at this stage no elution of GPC and GPE occurs.

The resin is then washed with water to give a very pure nGPC+mGPE solution which is separated by elution on basic resins. The amount of acid resin may be significantly reduced with a preventive partial purification of the crude deacylated mixture by extraction with water:alcohols, preferably $C_3$-$C_4$ alcohols as shown in Example 8.

When only pure GPC is desired, it could be convenient to remove phosphatidylethanolamine (PE) from alcoholic extracts of lecithins by elution on basic resins, before the treatment with sodium or potassium alcoholate. Pure GPC is so obtained after the purification of the crude deacylated mixture, as shown in Example 7. Even though the elimination of PE involves an additional elution on resin, it allows however to obtain a pure GPC aqueous solution at a much higher concentration than that normally obtained, since a lower amount of acid resin is used and GPC/GPE separation in aqueous medium is no longer required. This makes the final concentration step of GPC easier without substantially changing the overall volume of alcohol. Of course, the described process may be used also for the purification of synthetic GPC and GPE.

EXAMPLE 1

Preparation of Deoleated Soy Lecithin 1 kg of crude soy lecithin was suspended in 3.5 l of acetone cooled at 5° C., the suspension was stirred at 5° C. for 30 minutes and then filtered. The residue was suspended in 2 l of acetone, stirred at 5° C. for 2 hours, then filtered and the residue was washed with 1 l acetone at room temperature. The solid was dried under vacuum at 35° C.

680 g of soy deoleated lecithin were obtained.

EXAMPLE 2

Preparation of GPC by Deacylation in Methanol of Deoleated Soy Lecithin

The suspension of deoleated soy lecithin (0.5 kg) in anhydrous methanol (2 l) containing $CH_3ONa$ (24 g) was stirred at room temperature for about 3 hours. The mixture was filtered, the residue was washed with methanol (3×50 ml); the filtrate was neutralized (pH≈6) with acetic acid (about 25 ml) then concentrated up to about 500 ml and the fatty acid was separated.

The methanol solution, after decoloration with 2 g of active charcoal, was charged on an Amberlyst ® 15 resin (550 ml in acid form) equilibrated in methanol. The resin is washed with methanol (1,5 l) up to elimination of impurities (TLC) (about 7'), the resin was then washed with water (about 1.2 l). The aqueous solution was treated twice with active charcoal (2 g). The aqueous solution (containing about 44 g of nGPC+mGPE) was first eluted on a IR 93 resin (120 ml), in OH form equilibrated in water and then on an IR 401 resin (120 ml in OH form) equilibrated in water and finally on an IRC50 resin (40 ml, in acidic form) equilibrated in water. The obtained solution was concentrated obtaining 26 g of pure GPC (water content 10.1% assay with $HClO_4$ in acetic acid 99.8%).

A very hygroscopic solid, having the following characteristics was obtained by crystallization from ethanol.
$[\alpha]_D = -2,92$ (c = 10% in water).
P% = 12, 18% (calc. 12.15%).
N% = 5,49% (calc. 5.58%).

EXAMPLE 3

Preparation of GPC by Deacylation in Methanol From Crude Soy Lecithin

The suspension of crude soy lecithin (1 kg) in methanol (4 l) containing $CH_3ONa$ (48 g) was stirred at room temperature (20°-22° C.) for 4 hours, and then it was treated as described in Example 2.

21 g of GPC (water content 15.3%) were obtained with a purity degree similar to that obtained in Examples 2 and 3 (The amount of GPC obtainable from crude soy lecithin largely depends on the kind the starting lecithin).

EXAMPLE 4

Preparation of GPC by Deacylation of the Methanol Extract of Deoleated Soy Lecithin A suspension of deoleated soy lecithin (125 g) in methanol (250 ml) was stirred at room temperature for 2 hours and it was then filtered washing the residue with methanol (25 ml). The residue was suspended in methanol (125 ml), stirred at room temperature for 2 hours, filtered and the residue was washed with methanol (25 ml). A third extraction was carried out using 125 ml of methanol. The methanol solutions were collected, $CH_3ONa$ (1,6 g) and diatomaceous earth (2 g) were added thereto and the mixture was stirred at room temperature for 4 hours. After filtration, the methanol solution was neutralized with acetic acid (pH≈6), then concentrated to small volume (about 125 ml). The upper fatty phase was separated, the methanol solution was treated with active charcoal (0.5 g) and then concentrated to 40 ml of residual volume; the separated fats were discarded and then the procedure of Example 2 was followed, using 140 ml of Amberlyst ®15, 30 ml of IR 93, 30 ml of IR 401 and 12 ml of IR C 50. 6 g of pure GPC (water content 8.1%) were obtained. Using 250 g of crude soy lecithin instead of soy lecithin and operating as in Example 5, 5.3 g of GPC (water content 15.1%) were obtained with a similar degree.

EXAMPLE 5

Preparation of GPC by Deacylation of the Ethanol Extract of Deoleated Soy Lecithin A suspension of deoleated soy (140 g) in ethanol (365 ml) was stirred at room temperature for 2 hours, after which the mixture was filtered washing the residue with ethanol (40 ml). A second and third extraction were carried out using each time 140 ml of ethanol for the extraction and 25 ml for washing. The ethanol solutions were pooled, $CH_3ONa$ (1.5 g), diatomaceaous earth (2 g) were added thereto and the mixture was stirred at room temperature for 4 hours. After filtration, the ethanol solution was neutralized with acetic acid (pH about 6), then concentrated to about 350 ml. The ethanol solution was decoloured with active charcoal (0,5 g) and then eluted on IR C 50 resin (70 ml) in acid form, equilibrated in ethanol. The resin was washed with ethanol (about 200 ml) till complete elimination of impurities in the eluted ethanol (TLC), the resin was then washed with water (150 ml). The aqueous solution (containing about 5.8 g of nGPC+mGPE with $\simeq 0.75$ and $m \simeq 0.25$) was treated as previously described. 4.9 g of pure GPC were obtained (water content 12.2%). Using 280 g of crude soy lecithin, 2.5 g of pure GPC (water content 16.1%) with a similar purity degree were obtained.

EXAMPLE 6

Preparation of GPC by Deacylation of Crude Egg Lecithin

Treating as in Example 5 a solution of 75 g of crude egg lecithin in 150 ml of methanol containing 1.8 g of $CH_3ONa$ and using 80 ml of Amberlyst ®15 resin equilibrated in methanol, 8.6 g of pure GPC (water content 16%) were obtained. Using a solution of 75 g of crude egg lecithin in 200 ml of ethanol containing 1.8 g of $CH_3ONa$ and using 160 ml of Amberlyst ®15 resin, or 160 ml of IR C50 resin both equilibrated in ethanol and then washed in ethanol, 8.1 g of pure GPC (water content 12.5%) were obtained.

EXAMPLE 7

Preparation of GPC

A suspension of deoleated soy lecithin (260 g) in methanol (520 ml) was stirred at room temperature for 1 hour, filtered and the residue was washed with methanol (30 ml). The residue was extracted twice with 260 ml of methanol and the methanol extracts were pooled. The mixture was decoloured with 2 g of active charcoal, then eluted on IR 120 resin (100 ml) in acid form, equilibrated in methanol, then on IR 401 resin (300 ml) in OH form, equilibrated in methanol and finally on IR C50 (30 ml) in acid form, equilibrated in methanol washing the resins in series with 300 ml of methanol; 3 g of $CH_3ONa$ were then added to the methanol solution, the mixture was stirred at room temperature for 4 h, neutralized with acetic acid (pH$\simeq$6), then concentrated and the upper fatty phase was discarded. The methanol phase containing impure GPC was eluted on Amberlyst ®15 resin (180 ml) in acid form, equilibrated in methanol. The resin was washed with methanol (about 200 ml) till complete removal of impurities in the eluted methanol and the resin was then washed with water (250 ml). The aqueous solution was treated twice with active charcoal (2×1 g), water was evaporated under reduced pressure, obtaining 13.2 g of GPC (water content 11.1%) with a purity degree similar to that obtained in the previous examples.

EXAMPLE 8

Preparation of GPC

The deacylated methanol solution separated from the fatty phase obtained according to Example 2 was concentrated to small volume.

Water (150 ml) was added to the residue and the residual methanol was distilled off. 100 ml of n-butanol were added to the aqueous solution under stirring at room temperature and, after 30 minutes, the mixture was left to stand for 3 hours. The lower phase was separated, decoloured twice with 5 g of active charcoal each, and then concentrated to obtain an oily residue. The residue was dissolved in a volume of methanol so as to obtain a water content in the final solution lower than 2% and the solution was treated as in Example 2 using 400 ml of Amberlyst ®15 resin, obtaining 26.5 g of pure GPC (water content 14.9%).

EXAMPLE 9

Preparation of Pure GPE

After separation of GPC, pure GPE is obtained by eluting with a 5% aqueous solution of acetic acid the basic resin used for the separation GPC/GPE and evaporating thereafter the solvent under reduced pressure.

From the preparation of Example 2, 25.6 g of pure GPE (water content 16.1%) were obtained, titer with $HClO_4$ in acetic acid=99.5% on dry substance.

A solid product having the following characteristics as obtained by crystallization of methanol/water $[\alpha]_D = -3.1$ (c=5% in $H_2O$), From the preparation of Example 3, 28 g. of GPE (water content 12.5) were obtained.

From the preparation of Example 4, 5.6 g of GPE (water content 18.1%) were obtained.

From the preparation of Example 5, 1.3 g of GPE (water content 15%) were obtained.

From the preparation of Example 6, 3.5 g of GPE (water content 16.3%) were obtained.

I claim:

1. A process for the purification of glycerylphosphorylcholine (GPC) and glycerylphosphorylethanolamine (GPE) from a crude alcoholic mixture thereof obtained by deacylating crude or deoleated soy or egg lecithin or alcoholic extracts thereof comprising:

a) charging said mixture on a resin in acid form having carboxylic acid or sulfonic anchor groups, the resulting supported mixture having the formula (nGPC)+mGPE)+pResin wherein n represents mmoles of GPC and has a value of 0-1;

m represents mmoles of GPE and has a value of 0-1;

and p represents mequivalents of resin and has a value of 3-6 a for strong cationic resin and 6-8 for a weak cationic resin;

b) washing said supported mixture with methanol, ethanol or a hydrated mixture thereof;

c) eluting said washed supported mixture with water to obtain an aqueous solution of nGPC+mGPE; and d) eluting said aqueous solution of nGPC+mGPE with a strong basic resin in OH form to separate purified GPE from purified GPC.

2. A process according to claim 1 in which the crude deacylated mixture is partially purified by treating an aqueous mixture thereof with an alcohol selected from propanol, isopropanol, n-butanol, sec-butanol and ter-butanol followed by separation of the resultant phases to obtain an alcoholic phase comprising the mixture nGPC+mGPE.

3. A process for the purification of glycerylphosphorylcholine (GPC) in which an alcoholic extract of lethicin is eluted on a basic resin in OH form in order to separate phosphatidylethanolamine, and the resultant eluate deacylated and subjected to the purification step of claim 1.

4. A process according to claim 1 in which the cationic resin is of a macroreticular type.

5. A process according to claim 1 in which purified GPE is obtained by eluting the basic resin used for the separation of the GPC/GPE mixture with dilute aqueous acetic acid followed by evaporation under reduced pressure.

* * * * *